United States Patent
Park et al.

(10) Patent No.: US 12,018,010 B2
(45) Date of Patent: Jun. 25, 2024

(54) METHOD FOR PREPARING EFINACONAZOLE USING IONIC LIQUID AS MEDIUM

(71) Applicant: Daebong Ls Co., Ltd., Incheon (KR)

(72) Inventors: Eun Ju Park, Hwaseong-si (KR); Hyun Ji, Siheung-si (KR); Ji Eun Lee, Busan (KR); Jin Oh Park, Seoul (KR)

(73) Assignee: Daebong Ls Co., Ltd., Incheon (KR)

( * ) Notice: Subject to any disclaimer, the term of this patent is extended or adjusted under 35 U.S.C. 154(b) by 275 days.

(21) Appl. No.: 17/428,415

(22) PCT Filed: Sep. 25, 2020

(86) PCT No.: PCT/KR2020/013162
§ 371 (c)(1),
(2) Date: Aug. 4, 2021

(87) PCT Pub. No.: WO2021/060948
PCT Pub. Date: Apr. 1, 2021

(65) Prior Publication Data
US 2022/0127245 A1     Apr. 28, 2022

(30) Foreign Application Priority Data
Sep. 26, 2019   (KR) .................. 10-2019-0118645

(51) Int. Cl.
*C07D 401/06*    (2006.01)
(52) U.S. Cl.
CPC .................... *C07D 401/06* (2013.01)
(58) Field of Classification Search
CPC .................................................. C07D 401/06
See application file for complete search history.

(56) References Cited

U.S. PATENT DOCUMENTS

2016/0376253 A1    12/2016   Attolino et al.

FOREIGN PATENT DOCUMENTS

| | | |
|---|---|---|
| CN | 108276381 A | 7/2018 |
| IN | 201741018119 A | 11/2018 |
| KR | 10-0339166 B1 | 4/2004 |
| KR | 10-2009-0036349 A | 4/2009 |
| KR | 10-2015-0075187 A | 7/2015 |
| WO | WO 2005/014583 A1 | 2/2005 |
| WO | WO 2016/079728 A1 | 5/2016 |
| WO | WO 2016/193917 A1 | 12/2016 |

OTHER PUBLICATIONS

International Search Report dated Jan. 15, 2021 for PCT/KR2020/013162.
Wilkes, Ionic Liquids in Synthesis, Second Edition, 2008, pp. 1-6, 34-45, ISBN 978-3-527-31239-9.
有機合成化学協会誌, 2005, vol. 63, No. 5, pp. 503-510.

*Primary Examiner* — Samantha L Shterengarts
*Assistant Examiner* — Karen Cheng
(74) *Attorney, Agent, or Firm* — Lee IP Law, P.C.

(57) ABSTRACT

The present invention relates to a novel method for preparing efinaconazole using an ionic liquid as a medium. The method includes subjecting 1-[[(2R,3S)-2-(2,4-difluorophenyl)-3-methyloxiranyl]methyl]-1H-1,2,4-triazole to a coupling reaction with 4-methylenepiperidine or an organic chemically acceptable salt thereof in the presence of a base and an ionic liquid compound. The base makes the 4-methylenepiperidine or organic chemically acceptable salt thereof anionic. The use of the ionic liquid in the method of the present invention prevents the formation of related substances, shortens the reaction time, and enables easy preparation of the final compound efinaconazole in high purity and yield on a large scale, compared to the use of organic solvents in conventional methods.

3 Claims, No Drawings

METHOD FOR PREPARING EFINACONAZOLE USING IONIC LIQUID AS MEDIUM

CROSS REFERENCE TO RELATED APPLICATIONS

This is the U.S. national phase application based on PCT Application No. PCT/KR2020/013162, filed Sep. 25, 2020, which is based on Korean Patent Application No. 10-2019-0118645, filed Sep. 26, 2019, the entire contents of all of which are hereby incorporated by reference.

TECHNICAL FIELD

The present invention relates to a novel method for preparing efinaconazole using an ionic liquid as a medium.

BACKGROUND ART

Onychomycosis is a disease caused by fungal infection of the nail to damage to the nail. Causative fungi of onychomycosis include dermatophytes, non-dermatophytic molds, and yeasts.

External antifungal agents are widely used to treat onychomycosis mainly caused by dermatophytes. Representative examples of such external antifungal agents include amorolfine, ciclopirox, and efinaconazole.

Among these external antifungal drugs, efinaconazole is formulated into solutions for topical application and is known to be more effective at least twice than existing agents for topical application. For these reasons, efinaconazole is widely used as a therapeutic agent for onychomycosis.

Thus, demand for efinaconazole is gradually increasing and various methods for preparing efinaconazole in an economical and efficient manner are being investigated.

In connection with this, an example of the prior art is disclosed in International Patent Publication WO2016079728 A1 (Patent Document 1), the entire disclosure of which is hereby incorporated by reference.

Patent Document 1 discloses a process for the preparation of efinaconazole using catalytic asymmetric cyanosilylation of 2-chloro-1-(2,4-difluorophenyl)ethan-1-one and including a total of five steps, as depicted below:

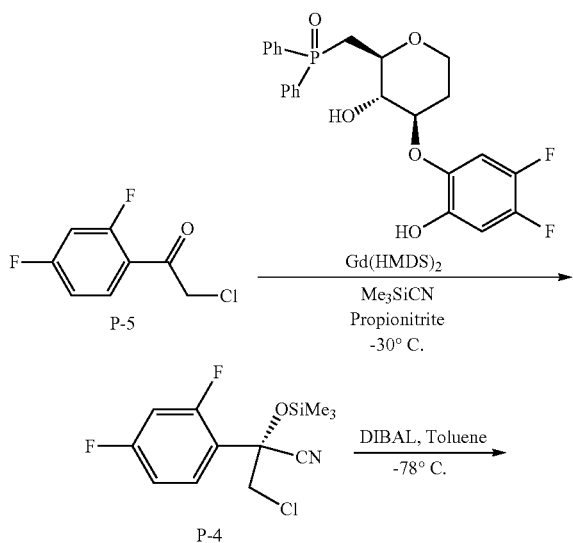

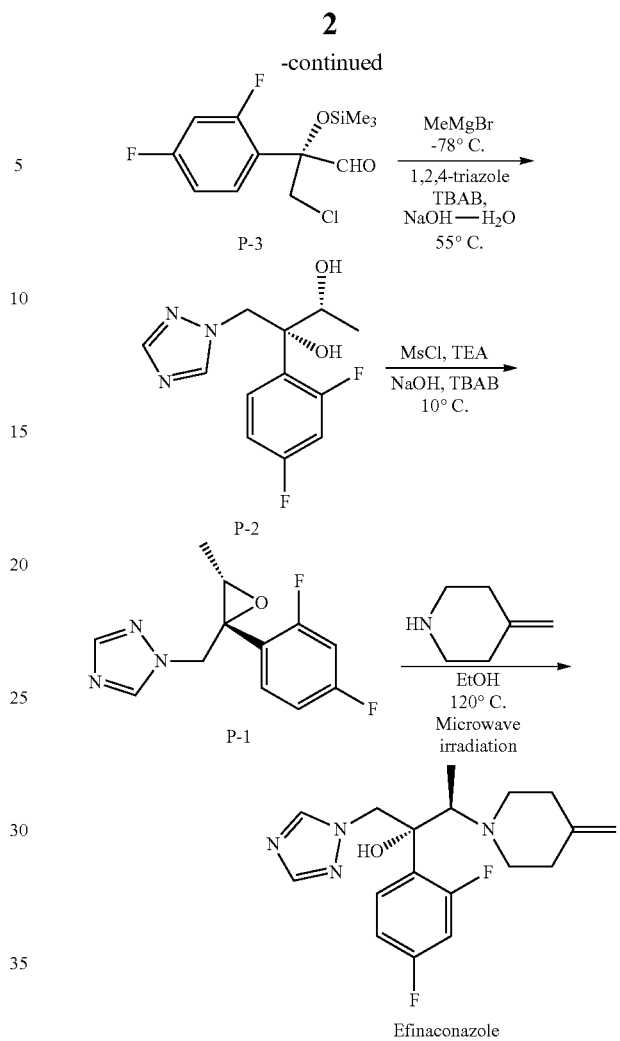

However, aside from the use of the expensive chiral ligand, the use of gadolinium bis(trimethylsilyl)amide is problematic: it is corrosive, reacts vigorously with air and water, and should be manipulated under anhydrous conditions. This process is therefore considered technically limited.

Furthermore, since the step of preparing efinaconazole employs microwave irradiation for coupling between P-1 and 4-methylenepiperidine hydrochloride at 120° C., the process is suitable for laboratory scale but is not efficient for mass production.

Therefore, there is a need to develop a process for preparing efinaconazole, a good antifungal agent used to treat onychomycosis, in high yield and purity in a safe and efficient manner on a large scale.

(Patent Document 1) WO2016079728 A1 (published on May 26, 2016)

DETAILED DESCRIPTION OF THE INVENTION

Problems to be Solved by the Invention

An object of the present invention is to provide a novel method for preparing efinaconazole using an ionic liquid compound as a reaction medium instead of a solvent whereby efinaconazole is synthesized in high purity and yield in an economical manner on a large scale while meeting the criteria for related substances.

Means for Solving the Problems

The present invention has been made in an effort to solve the problems of the prior art and provides a method for preparing efinaconazole including subjecting 1-[[(2R,3S)-2-(2,4-difluorophenyl)-3-methyloxiranyl]methyl]-1H-1,2,4-triazole to a coupling reaction with 4-methylenepiperidine or an organic chemically acceptable salt thereof in the presence of a base and an ionic liquid compound.

The ionic liquid compound is selected from compounds represented by Formulae III to VII:

[Formula III]

wherein each R1 is hydrogen, methyl or ethyl and X is Cl, Br, $BF_4$, $PF_6$, trifluoromethanesulfonate (OTf), acetate (OAc), methanesulfonate or $C_1$-$C_3$ alkyl sulfate;

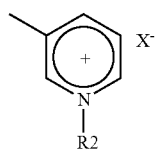

[Formula IV]

wherein R2 is hydrogen or $C_1$-$C_{12}$ alkyl and X is as defined in Formula III;

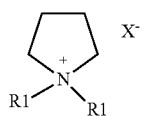

[Formula V]

wherein R1 and X are as defined in Formula III;

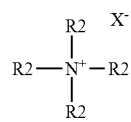

[Formula VI]

wherein R2 is as defined in Formula IV and X is as defined in Formula III; and

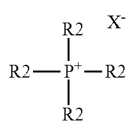

[Formula VII]

wherein R2 is as defined in Formula IV and X is as defined in Formula III, and mixtures thereof.

The ionic liquid compound is selected from 1-ethyl-3-methylimidazolium bromide, 1-ethyl-3-methylimidazolium hexafluorophosphate, N-butyl-N-methylpyrrolidinium bromide, N-butyl-N-methylpyrrolidinium hexafluorophosphate, N-butyl-3-methylpyridinium bromide, N-butyl-3-methylpyridinium hexafluorophosphate, tetra-N-butylammonium bromide, tetra-N-butylammonium hexafluorophosphate, tetra-N-butylphosphonium bromide, tetra-N-butylphosphonium hexafluorophosphate, and mixtures thereof.

The ionic liquid compound is an imidazolium alkyl sulfate.

The ionic liquid compound is 1-ethyl-3-methylimidazolium ethyl sulfate.

The base is selected from the group consisting of potassium t-butoxide, sodium t-butoxide, NaH, NaOH, KOH, and mixtures thereof.

Effects of the Invention

The use of the ionic liquid in the method of the present invention prevents the formation of related substances, shortens the reaction time, and enables easy preparation of the final compound efinaconazole in high purity and yield on a large scale, compared to the use of organic solvents in conventional methods.

BEST MODE FOR CARRYING OUT THE INVENTION

The present invention will now be described in detail.

The present invention provides a method for preparing efinaconazole including subjecting 1-[[(2R,3S)-2-(2,4-difluorophenyl)-3-methyloxiranyl]methyl]-1H-1,2,4-triazole to a coupling reaction with 4-methylenepiperidine or an organic chemically acceptable salt thereof in the presence of a base and an ionic liquid compound.

The compound 1-[[(2R,3S)-2-(2,4-difluorophenyl)-3-methyloxiranyl]methyl]-1H-1,2,4-triazole is represented by Formula I:

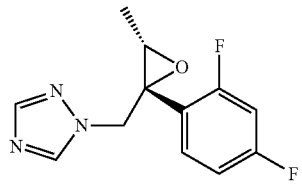

[Formula I]

The compound represented by Formula I is a key intermediate for triazole antifungal therapeutic agents such as voriconazole, ravuconazole, albaconazole, and efinaconazole. The compound represented by Formula I can be converted into various derivatives via various nucleophilic substitution reactions due to the chirality at C2 and C3 of the oxirane ring. The compound represented by Formula I can be prepared according to the methods known in the literature, e.g., WO2016079728 and WO2005014583. The compound represented by Formula I is also commercially available.

The compound 4-methylenepiperidine is represented by Formula II:

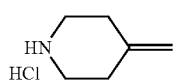

[Formula II]

This compound acts as a nucleophile for the ring opening at C3 of the oxirane ring and is commercially available. The 4-methylenepiperidine can exist in the form of various organic chemical salts, mainly a hydrochloride.

The 4-methylenepiperidine or salt thereof can be used in a molar ratio of 1:1 to 20:1, preferably 5:1 to 15:1, relative to the 1-[[(2R,3S)-2-(2,4-difluorophenyl)-3-methyloxiranyl]methyl]-1H-1,2,4-triazole.

The base serves to make the 4-methylenepiperidine anionic. Any base that can make the reaction conditions basic may be used without limitation. The base is selected from the group consisting of potassium t-butoxide, sodium t-butoxide, NaH, NaOH, KOH, and mixtures thereof.

The base is used in an amount of 2 to 20 times, preferably 5 to 15 times the amount of the 4-methylenepiperidine used. If the equivalent amount of the base is less than the lower limit defined above, the reaction may not be completed. Meanwhile, if the equivalent amount of the base exceeds the upper limit defined above, a large amount of impurities may be produced.

The ionic liquid compound refers to a material that cannot form a crystal due to the size asymmetry of the cation and anion and exists in a liquid state. Particularly, a room temperature ionic liquid (RTIL) refers to an ionic liquid that exists as a liquid at room temperature. A representative ionic liquid compound is a molten salt composed of a nitrogen-containing organic cation having a ring structure and an inorganic anion having a smaller size than the cation.

The ionic liquid compound is characterized by low volatility, good thermal stability, high ionic conductivity, wide electrochemical stability window, and low vapor pressure. Due to these characteristics, the ionic liquid compound can be used as a stable and eco-friendly solvent to replace an organic solvent. That is, the use of the ionic liquid compound that can replace an organic solvent or significantly reduce its amount solves processing or environmental problems encountered in the use of an organic solvent.

If the compound of Formula I is subjected to a coupling reaction with the compound of Formula II in the absence of the ionic liquid compound, various kinds of impurities are generated in excess, the reaction time is greatly lengthened (for example, the purity of the final product is only around 50% or at least 15% of the starting material p-1 remains unreacted, indicating that the reaction is not completed), larger amounts of the raw materials and the base are required (for example, 15 equivalents of 4-MH as an amine reagent are required), and additional processes such as column purification are required, resulting in an increase in the overall processing time.

If the reaction is not completed for a very long time or side reactions take place, there is a risk that related substances may be produced.

In contrast, the addition of the ionic liquid for the reaction in the method of the present invention relatively reduces the amount of the base used, shortens the reaction time, substantially prevents the formation of impurities, and ensures a much higher yield than those in other known reactions. According to the method of the present invention, when the reaction mixture has a purity of 80% or more and is crystallized from 60% ethanol without column purification, the final product efinaconazole can be obtained in a high yield of at least 99.8%, preferably in quantitative yield (100%). In addition, the use of the base can be greatly reduced. For example, only 7 equivalents of 4-Ml as the base may be used. In conclusion, the method of the present invention is very economical and is suitable for mass production.

The ionic liquid compound is selected from imidazolium, pyridinium, pyrrolidinium, ammonium, and phosphonium compounds, which are represented by Formulae III to VII, respectively:

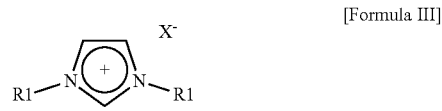

[Formula III]

wherein each k is hydrogen, methyl or ethyl and X is Cl, Br, $BF_4$, $PF_6$, trifluoromethanesulfonate (OTf), acetate (OAc), methanesulfonate or $C_1$-$C_3$ alkyl sulfate;

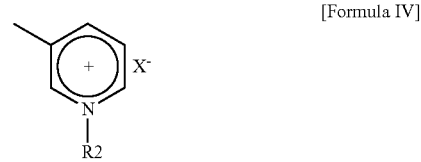

[Formula IV]

wherein R2 is hydrogen or $C_1$-$C_{12}$ alkyl and X is as defined in Formula III;

[Formula V]

wherein R1 and X are as defined in Formula III;

[Formula VI]

wherein R2 is as defined in Formula IV and X is as defined in Formula III; and

[Formula VII]

wherein R2 is as defined in Formula IV and X is as defined in Formula III, and mixtures thereof.

In Formulae III to VII, X is more specifically selected from the group consisting of 1-ethyl-3-methylimidazolium ethyl sulfate, 1-ethyl-3-methylimidazolium tetrafluoroborate, 1-ethyl-3-methylimidazolium tosylate, 1-ethyl-3-methylimidazolium methanesulfonate, 1-ethyl-3-methylimidazolium triflate, 1-ethyl-3-methylimidazolium dicyanamide, 1-butyl-3-methylimidazolium tetrafluoroborate, 1-butyl-3-methylimidazolium bis(trifluoromethylsulfonyl)imide, 1-butyl-3-methylimidazolium dicyanamide, 1-butyl-3-methylimidazolium triflate, 1-butyl-3-methylimidazolium methanesulfonate, 1-butyl-3-methylimidazolium trifluoromethanesulfonate, 1,3-didecyl-2-methylimidazolium bis(trifluoromethylsulfonyl)imide, amyltriethylammonium bis(trifluoromethylsulfonyl)imide, 1-butyl-2,3-dimethylimidazolium triflate, 1-butyl-2,3-dimethylimidazolium tetrafluoroborate, 1-(2-hydroxyethyl)-3-methylimidazolium tetrafluoroborate, 1-decyl-3-methylimidazolium tetrafluoroborate, 1-butyl-3-methylpyridinium tetrafluoroborate, 1-butyl-4-methylpyridinium tetrafluoroborate, 1-allyl-3-ethylimidazolium tetrafluoroborate, 1-methyl-1-propylpiperidinium bis(trifluoromethylsulfonyl)imide, methyltrioctylammonium bis(trifluoromethylsulfonyl)imide, butyltrimethylammonium bis(trifluoromethylsulfonyl)imide, triethylsulfonium bis(trifluoromethylsulfonyl)imide, and diethylmethylsulfonium bis(trifluoromethylsulfonyl)imide, more preferably 1-ethyl-3-methylimidazolium methanesulfonate, 1-butyl-3-methylimidazolium tetrafluoroborate, 1-butyl-3-methylimidazolium bis(trifluoromethylsulfonyl)imide, 1-butyl-3-methylimidazolium methanesulfonate, 1-butyl-3-methylimidazolium trifluoromethanesulfonate, 1,3-didecyl-2-methylimidazolium bis(trifluoromethylsulfonyl)imide, amyltriethylammonium bis(trifluoromethylsulfonyl)imide, 1-butyl-2,3-dimethylimidazolium tetrafluoroborate, 1-allyl-3-ethylimidazolium tetrafluoroborate, methyltrioctylammonium bis(trifluoromethylsulfonyl)imide or butyltrimethylammonium bis(trifluoromethylsulfonyl)imide, most preferably 1-butyl-3-methylimidazolium tetrafluoroborate, 1-butyl-3-methylimidazolium trifluoromethanesulfonate, amyltriethylammonium bis(trifluoromethylsulfonyl)imide, 1-allyl-3-ethylimidazolium tetrafluoroborate or a mixture thereof.

The ionic liquid compound is preferably 1-ethyl-3-methylimidazolium bromide, 1-ethyl-3-methylimidazolium hexafluorophosphate, N-butyl-N-methylpyrrolidinium bromide, N-butyl-N-methylpyrrolidinium hexafluorophosphate, N-butyl-3-methylpyridinium bromide, N-butyl-3-methyl pyridinium hexafluorophosphate, tetra-N-butylammonium bromide, tetra-N-butylammonium hexafluorophosphate, tetra-N-butylphosphonium bromide, tetra-N-butylphosphonium hexafluorophosphate, most preferably 1-ethyl-3-methylimidazolium ethyl sulfate.

The amount of the ionic liquid compound is 3 to 20 times, preferably 3 to 10 times the amount of the 1-[[(2R,3S)-2-(2,4-difluorophenyl)-3-methyloxiranyl]methyl]-1H-1,2,4-triazole.

For example, efinaconazole may be easily synthesized in high purity and yield according to the following reaction scheme:

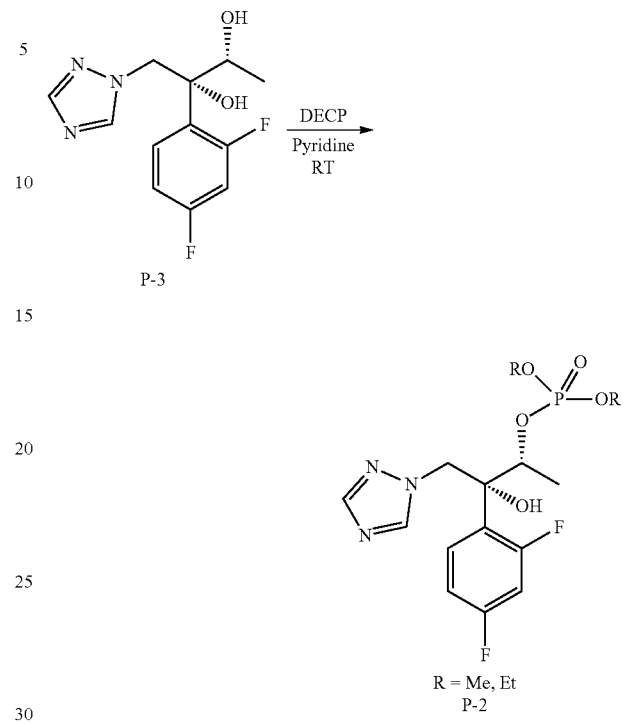

As depicted in Reaction 1, diethyl chlorophosphate is added dropwise to (2R,3R)-2-(2,4-difluorophenyl)-1-(1H-1,2,4-triazol-1-yl)butane-2,3-diol as a starting material in pyridine as a solvent. The reaction is allowed to proceed at room temperature for 2 hours to obtain a dimethyl or diethyl phosphate intermediate P-2. No solvent other than pyridine is used in the reaction. For example, the phosphate leaving group may be a dimethyl phosphoryl or diethyl phosphoryl group. A diethyl phosphoryl group is most preferably used. For example, potassium t-butoxide (KOt-Bu), NaOH, KOH, TEA or DIPEA may be used as a base in the reaction for the preparation of the new diethyl phosphate intermediate. Pyridine is most preferably used. The reaction is carried out at a temperature of 20 to 30° C. The reaction can be completed within 3 hours at room temperature.

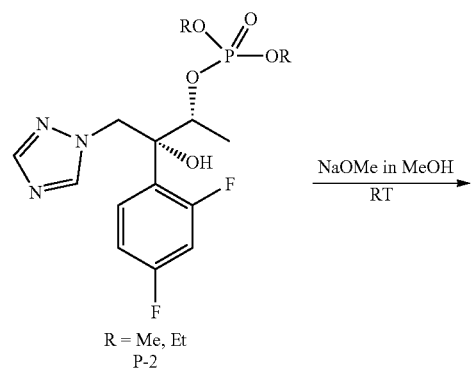

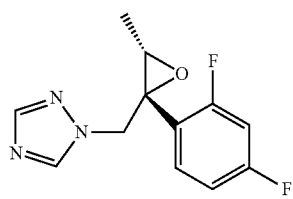

P-1

As depicted in Reaction 2, a solution of sodium methoxide in methanol is added dropwise to the dimethyl or diethyl phosphate intermediate. The reaction is allowed to proceed at room temperature for 2 hours to obtain a compound P-1. No solvent is used in the reaction.

[Reaction 3]

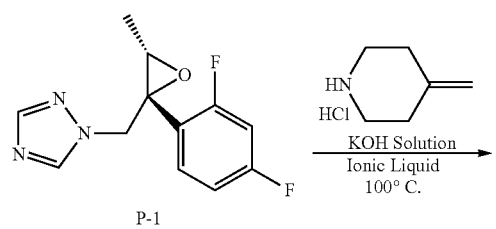

P-1

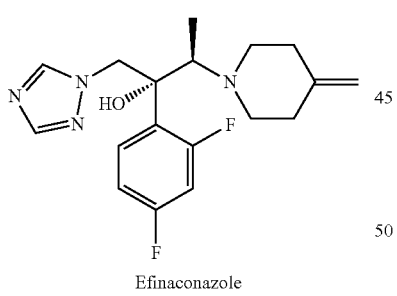

Efinaconazole

As depicted in Reaction 3, 4-methylenepiperidine is added dropwise to the compound P-1 in the presence of 1-ethyl-3-methylimidazolium ethyl sulfate as an ionic liquid instead of an organic solvent. The reaction is completed within 6 hours at 100° C. The ionic liquid is used in an amount of 3 to 10 times, preferably 5 to 10 times the amount of the compound P-1.

The present invention will be more specifically explained with reference to the following examples. However, these examples are provided for illustrative purposes only and are not intended to limit the scope of the invention.

Example 1

Synthesis of (2R,3R)-3-(2,4-difluorophenyl)-3-hydroxy-4-(1H-1,2,4-triazol-1-yl)butan-2-yl dimethyl phosphate

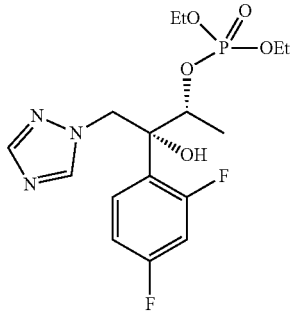 [SMILES: CCOP(=O)(OCC)O[C@H](C)[C@](O)(Cn1cncn1)c1ccc(F)cc1F]

10 g of (2R,3R)-2-(2,4-difluorophenyl)-1-(1H-1,2,4-triazol-1-yl)butane-2,3-diol and 50 ml of pyridine were placed in a flask. The mixture was stirred at room temperature (23-28° C.) for 10 min. After dropwise addition of 7.20 ml of diethyl chlorophosphite, stirring was continued at room temperature for 2 h to afford 14.3 g (95%) of (2R,3R)-3-(2,4-difluorophenyl)-3-hydroxy-4-(1H-1,2,4-triazol-1-yl)butan-2-yl diethyl phosphate. The product was directly used in the subsequent reaction without further work-up.

Synthesis of 1-[[(2R,3S)-2-(2,4-difluorophenyl)-3-methyloxiranyl]methyl]-1H-1,2,4-triazole

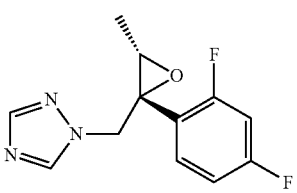 [SMILES: C[C@@H]1O[C@@]1(Cn1cncn1)c1ccc(F)cc1F]

14.4 ml of a solution of sodium methoxide was added to the (2R,3R)-3-(2,4-difluorophenyl)-3-hydroxy-4-(1H-1,2,4-triazol-1-yl)butan-2-yl diethyl phosphate. The mixture was stirred at room temperature (23-28° C.) for 2 h. After completion of the reaction, the reaction mixture was worked up with ethyl acetate and distilled water. The organic layer was collected, dried over sodium sulfate, filtered, and concentrated under reduced pressure to afford 7.98 g (90%) of 1-[[(2R,3S)-2-(2,4-difluorophenyl)-3-methyloxiranyl]methyl]-1H-1,2,4-triazole.

$^1$H NMR (400 MHz, CDCl$_3$) δ 1.64 (3H, d), 3.19 (1H, q), 4.41-4.48 (1H, m), 4.85-4.92 (1H, m), 6.69-6.83 (2H, m), 6.96-7.07 (1H, m), 7.81 (1H, s), 7.98 (1H, s)

Synthesis of (2R,3R)-2-(2,4-difluorophenyl)-3-(4-methylenepiperidin-1-yl)-1-(1H-1,2,4-triazol-1-yl)butan-2-ol

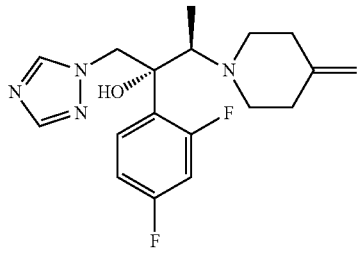

Efinaconazole 42.44 g of 4-methylenepiperidine hydrochloride was mixed with 354.01 ml of an aqueous solution of 50% potassium hydroxide. The mixture was stirred at room temperature (23-28° C.) for 2 h. To the reaction mixture was added 638.4 ml of ethyl ether. After 30 min stirring, the resulting mixture was left standing for layer separation. 638.4 ml of purified water was added to the organic layer. Stirring was continued for 30 min. After layer separation, the organic layer was concentrated. To the concentrate were added 7.98 g of the 1-[[(2R,3S)-2-(2,4-difluorophenyl)-3-methyloxiranyl]methyl]-III-1,2,4-triazole, 95.76 ml of purified water, and 40 ml of 1-ethyl-3-methylimidazolium ethyl sulfate as an ionic liquid. The mixture was stirred at 100° C. for 6 h. After the completion of the reaction was confirmed, the reaction mixture was cooled to room temperature and 638.4 ml of ethyl acetate and 638.4 ml of purified water were added thereto. The resulting mixture was stirred and allowed to stand for layer separation. 638.4 ml of a saturated aqueous solution of sodium chloride was added to the organic layer, followed by stirring for 30 min. The organic layer was separated, dried over anhydrous sodium sulfate, filtered, concentrated under reduced pressure to remove the organic solvent, and crystallized to give 8.85 g (80%) of the title compound.

$^1$H NMR (400 MHz, CDCl$_3$) δ 0.96 (3H, dd), 2.1-2.5 (61H, m), 2.6-2.8 (2H, m), 2.91 (1H, q), 4.64 (2H, s), 4.80 (1H, d), 4.89 (1H, d), 5.48 (1H, brs), 6.7-6.8 (2H, m), 7.47-7.63 (1H, m), 7.79 (1H, s), 8.03 (1H, s)

Comparative Example 1—Preparation of Efinaconazole According to the Method Described in Korean Patent No. 10-0339166

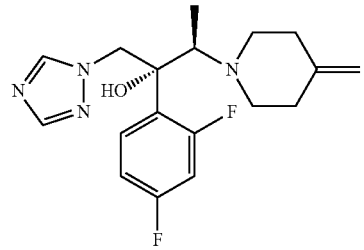

Efinaconazole 11.2 ml of an aqueous solution of 50% potassium hydroxide was added to 1.336 g of 4-methylenepiperidine hydrochloride. The mixture was dissolved with stirring. The solution was extracted three times with 20 ml of ethyl ether, followed by removal of the ethyl ether from the organic layer. To the residue were sequentially added 3 ml of ethanol, 251 mg of the oxirane intermediate (1-[[(2R,3S)-2-(2,4-difluorophenyl)-3-methyloxiranyl]methyl)]-1H-1,2,4-triazole) synthesized in the same manner as in Example 1, and 3 ml of distilled water. The mixture was heated to reflux at 85° C. for 24 h. After completion of the reaction, the reaction solution was cooled to room temperature and 20 ml of ethyl acetate and 20 ml of distilled water were added thereto. The organic phase was separated and the aqueous phase was extracted three times with 20 ml of ethyl acetate. The organic layer was collected, washed with brine, dried over anhydrous magnesium sulfate, concentrated under reduced pressure to remove the solvent, and purified by column chromatography to give 188 mg (54.0%) of the title compound.

The invention claimed is:

1. A method for preparing efinaconazole, the method comprising subjecting 1-[[(2R, 3 S)-2-(2,4-difluorophenyl)-3-methyl oxiranyl]methyl]-1H-1,2,4-triazole to a coupling reaction with 4-methylenepiperidine or an organic chemically acceptable salt thereof in the presence of a base and an ionic liquid compound,
    wherein the ionic liquid compound is an imidazolium alkyl sulfate.

2. The method according to claim 1, wherein the ionic liquid compound includes 1-ethyl-3-methylimidazolium ethyl sulfate.

3. The method according to claim 1, wherein the base includes potassium t-butoxide, sodium t-butoxide, NaH, NaOH, KOH, or mixtures thereof.

* * * * *